(12) United States Patent
Stoll et al.

(10) Patent No.: US 12,426,928 B2
(45) Date of Patent: Sep. 30, 2025

(54) EXTENDED TAB SEPARATION APPARATUS AND METHOD

(71) Applicant: Zimmer Biomet Spine, Inc., Westminster, CO (US)

(72) Inventors: Caleb Lee Stoll, Broomfield, CO (US); Randall G. Mast, Denver, CO (US); Allison Christine Capote, Boulder, CO (US); Heidi Farmer, Lafayette, CO (US); Guillaume Quetier, Lakewood, CO (US); Daniel Burke, Thornton, CO (US)

(73) Assignee: Highridge Medical, LLC, Westminster, CO (US)

( * ) Notice: Subject to any disclaimer, the term of this patent is extended or adjusted under 35 U.S.C. 154(b) by 0 days.

(21) Appl. No.: 18/742,980

(22) Filed: Jun. 13, 2024

(65) Prior Publication Data

US 2024/0325060 A1  Oct. 3, 2024

Related U.S. Application Data

(63) Continuation of application No. 17/382,518, filed on Jul. 22, 2021, now Pat. No. 12,029,454.

(60) Provisional application No. 63/054,968, filed on Jul. 22, 2020.

(51) Int. Cl.
*A61B 17/70* (2006.01)
*A61B 17/00* (2006.01)

(52) U.S. Cl.
CPC ...... *A61B 17/7091* (2013.01); *A61B 2017/00477* (2013.01); *A61B 2017/00876* (2013.01)

(58) Field of Classification Search
CPC .................................... A61B 17/7074–7092
See application file for complete search history.

(56) References Cited

U.S. PATENT DOCUMENTS

| | | | |
|---|---|---|---|
| 10,806,498 B2 * | 10/2020 | Erramilli | A61B 17/7079 |
| 2014/0094854 A1 * | 4/2014 | Schwab | A61B 17/7022 606/279 |
| 2016/0346017 A1 * | 12/2016 | Meyer | A61B 17/8863 |
| 2018/0235677 A1 * | 8/2018 | Kam | A61B 17/7032 |
| 2020/0261124 A1 * | 8/2020 | Peterson | A61B 17/7086 |
| 2021/0220023 A1 * | 7/2021 | Glaser | A61B 17/8883 |
| 2021/0236178 A1 * | 8/2021 | McBride | A61B 17/7082 |
| 2022/0240990 A1 * | 8/2022 | Kim | A61B 17/7032 |

* cited by examiner

*Primary Examiner* — Eduardo C Robert
*Assistant Examiner* — Steven J Cotroneo

(57) ABSTRACT

A tool for breaking tabs of a vertebral bone anchor can include a tip, a first rail, and a second rail. The tip can be positionable over a housing of a vertebral bone anchor. The first rail can be pivotably coupled to the tip and can extend proximally away from the tip. The first rail can be configured to receive a first extended tab therein. The first rail can be pivotable with respect to the tip between a first upright position and a first outward position to break the first extended tab from the housing. The second rail can be pivotably coupled to the tip and can extend proximally away from the tip.

20 Claims, 9 Drawing Sheets

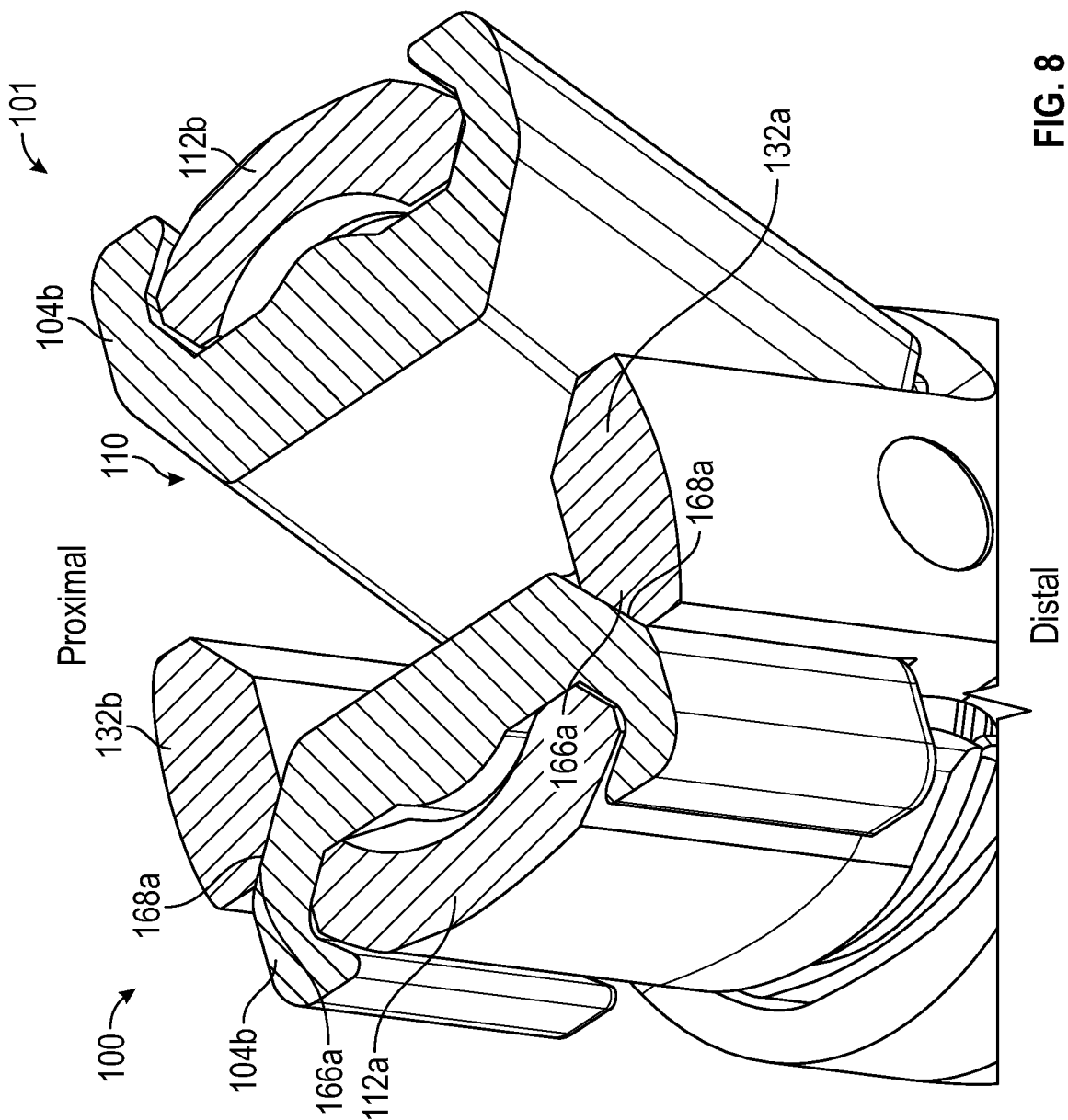

EXTENDED TAB SEPARATION APPARATUS AND METHOD

CLAIM OF PRIORITY

This application is a continuation of U.S. application Ser. No. 17/382,518, filed Jul. 22, 2021, now U.S. Pat. No. 12,029,454, which claims the benefit of U.S. Provisional Patent Application Ser. No. 63/054,968, filed on Jul. 22, 2020, the benefit of priority of which is claimed hereby, and which is incorporated by reference herein in its entirety.

BACKGROUND

Orthopedic devices such as rods, plates, tethers, staples, and other devices can be used in various spinal procedures to correct abnormalities (e.g., scoliosis) or to address injuries (e.g., vertebral fracture). In some spinal procedures, anchors and rods can be secured along a spinal column between one or more vertebrae to stabilize a region of the spine. Some surgical procedures performed on the spinal column using such devices have become less invasive, in part because specialty tools exist to help reduce invasiveness.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8 illustrates a cross-sectional isometric view of a portion of a tab breaker system.

DETAILED DESCRIPTION

Bone anchors can be used together with connecting members (such as rigid and semi-rigid rods) to straighten a region of a human spine to address an abnormality (e.g., scoliosis), to stabilize a spine following an injury (e.g., fractured vertebrae), or to address degeneration of the spine caused by disease. In minimally invasive spinal procedures to address these issues, multiple small incisions can be made to form multiple small cavities near individual vertebrae. A large amount of the procedure is performed through manipulation of instruments and components extending through the small surgical cavities using special instruments that are able to be manipulated from outside of the cavities. For example, anchors are commonly driven into vertebrae, where the anchors can include extended tabs coupled to the anchors and having a length sufficient to extend outside of the cavity so that the anchors (and components engaging the anchors) can be manipulated from outside of the cavities. Because the extended tabs comprise a length sufficient to extend through the cavities, they must be separable from heads of the anchors when the heads are secured to vertebrae.

Some designs include two extended tabs coupled to the head of the anchor at a breakaway portion, where each extended tab can be individually bent to allow separation of the extension from the head at the breakaway portions. This design requires relative movement of the extended tabs for separation. However, in some procedures, forces must be transferred from a portion of the extended tabs external to the cavity to a portion of the extended tabs internal to the cavity and ultimately to the head and/or shank of the anchor within the cavity. Therefore, it is desirable to have an extended tab connected to the anchor head that is capable of transferring forces but is also easily separable from the head of the anchor.

This disclosure helps to address these challenges by providing anchors with relative rigid connections to the anchor head while providing a device to help to easily separate the extended tabs from the head. Such separation can be performed using a double tab breaker including multiple handles and dual action for fast operation with reduced applied force.

The above discussion is intended to provide an overview of subject matter of the present patent application. It is not intended to provide an exclusive or exhaustive explanation of the invention. The description below is included to provide further information about the present patent application.

Figure 1C:
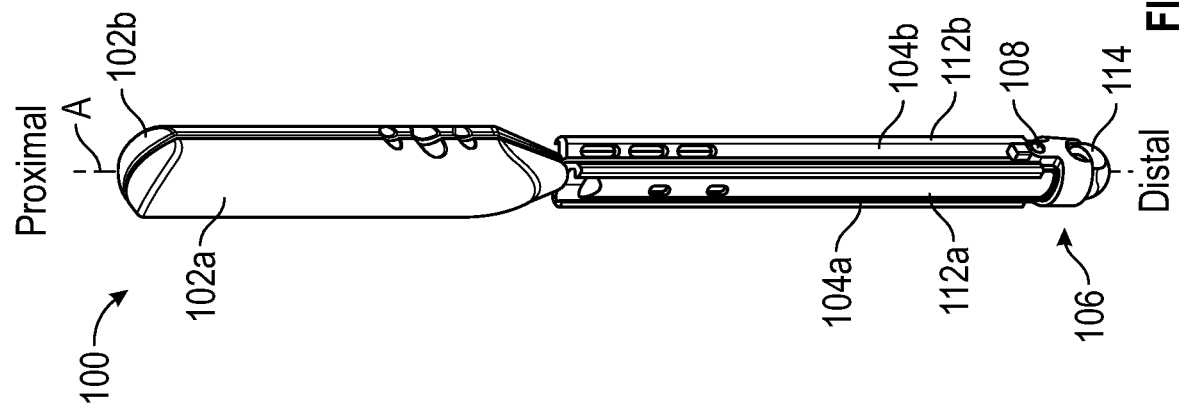
FIG. 1C illustrates an isometric view of a tab breaker system.
Figure 1B:
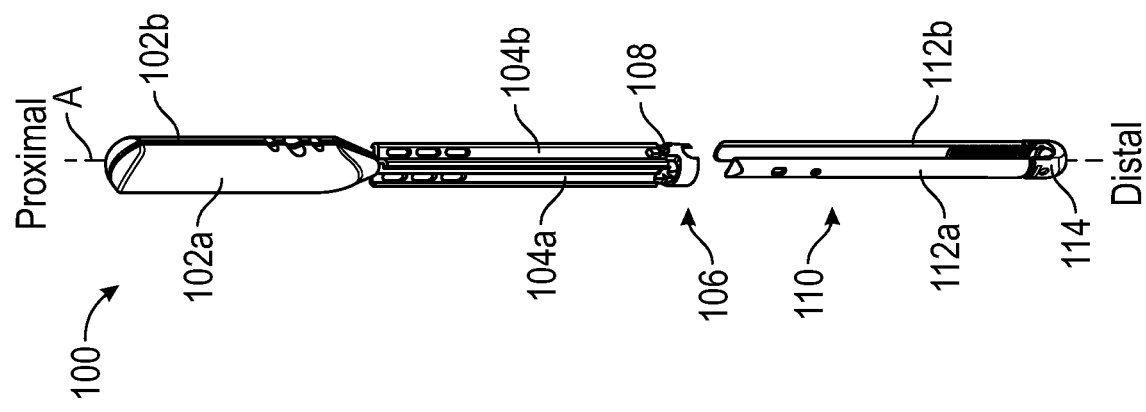
FIG. 1B illustrates an isometric view of a tab breaker system.
Figure 1A:
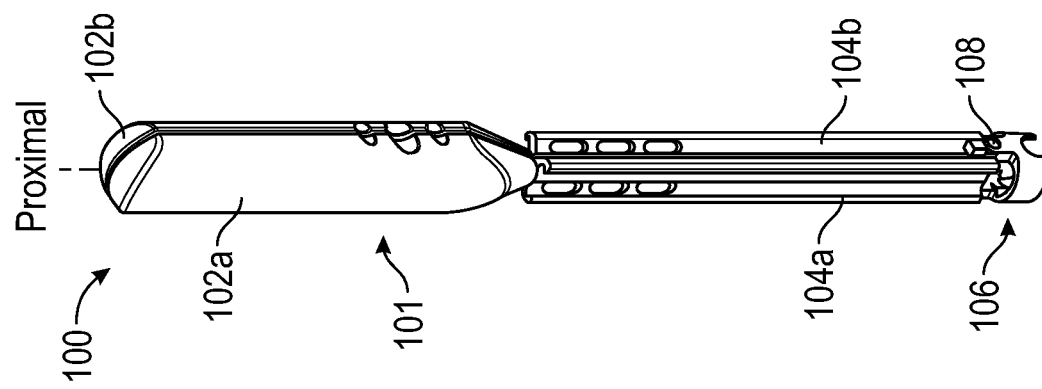
FIG. 1A illustrates an isometric view of a tab breaker system.

FIG. 1A illustrates an isometric view of a tab breaker system 100. FIG. 1B illustrates an isometric view of the tab breaker system 100. FIG. 1C illustrates an isometric view of the tab breaker system 100. FIGS. 1A-1C are discussed together below.

The tab breaker system 100 can include a tab breaker 101 that can include handles 102a and 102b (collectively referred to has handles 102), rails 104a and 104b (collectively referred to as rails 104), and a tip 106, which can include a pivot 108. As shown in FIG. 1B, the system 100 can also include an anchor 110. The anchor 110 can include extended tabs 112a and 112b (collectively referred to as extended tabs 112 or tabs 112), and a head 114. FIGS. 1A-1C also show orientation indicators Proximal and Distal and Axis A.

The tab breaker 101 can be a tool for breaking tabs off anchors, as discussed in further detail below. The handles 102, rails 104, and the tip 106 can be made of rigid and semi-rigid materials such as metals, plastics, composites, or the like.

The anchor 110 can generally be a vertebral anchor or bone anchor such as for securing to a vertebra of a patient's spine. The anchor 110 can be comprised of bio-compatible materials, such as one or more of stainless steel, titanium, cobalt-chromium, or the like. In some examples, the anchor 110 can be comprised of only one material, and can be comprised of multiple materials in other examples.

Figure 2:
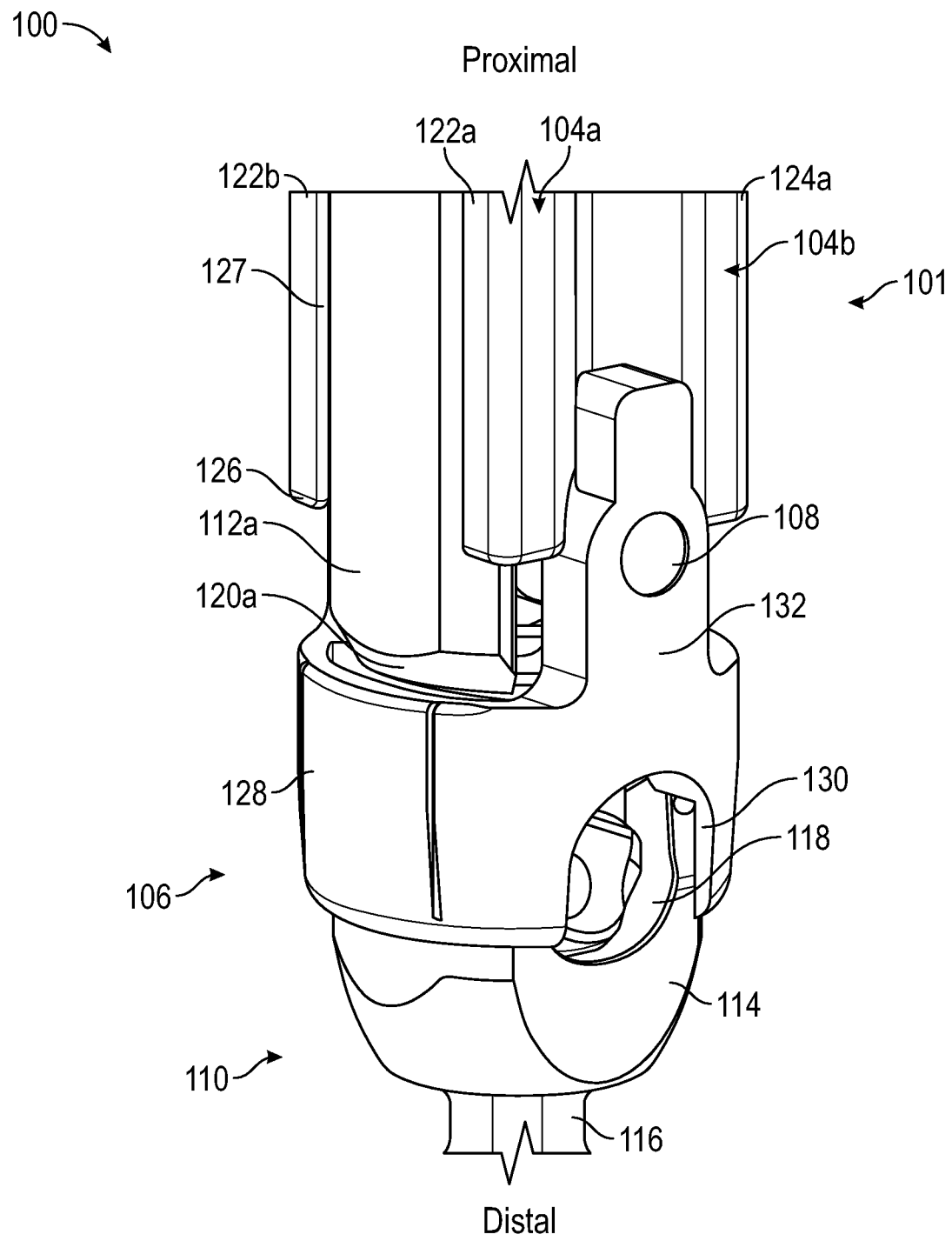
FIG. 2 illustrates a focused isometric view of a tab breaker system.

The head 114 of the anchor 110 can be coupled to a shank, as shown in FIG. 2. The extended tabs 112A and 112B can extend substantially proximally from the head 114 and substantially parallel to axis A. Together, the extended tabs 112A and 112B can form an incomplete hollow cylinder separated by anchor slots. The extended tabs 112A and 112B can be coupled to the head 114 by break off portions, as discussed below.

The handles 102 can extend generally along the axis A and can be sized and shaped to be grasped and actuated or operated. That is, the handles 102 can be rounded or contoured for ergonomic operation thereof.

The rails 104a and 104b can extend along the axis A and can be connected to a distal portion of the handles 102a and 102b, respectively, at a proximal portion of the rails 104a and 104b, respectively. A distal portion of the rails 104a and 104b can be connected to a proximal portion of the tip 106. In some examples, the rails 104a and 104b can be connected to the tip 106 by the pivot 108. The rails 104a and 104b can be configured to receive the extended tabs 112a and 112b, respectively. The tip 106 can be annular or oval-shaped and can be positionable on or over the housing 114 such that the tip 106 can be configured to receive at least a portion of the head 114 of the anchor 110 therein.

During a procedure, the tab breaker can be provided, as shown in FIG. 1A, with the handles 102 and rails 104 together or connected and the tip 106 oriented distally. The rails 104a and 104b can be moved distally, as shown in FIG. 1B to receive the extended tabs 112a and 112b into the rails 104a and 104b, respectively. The extended tabs 112a and 112b can be translated into the rails 104a and 104b, respectively, until the head 114 is received into the tip 106 and contacts the tip 106, as shown in FIG. 1C.

The rails 104a and 104b can be configured to retain the extended tabs 112a and 112b therein, respectively, such that the rails 104a and 104b limit movement of the extended tabs 112a and 112b with respect to the rails 104a and 104b, respectively, except for translation of the tabs 112a and 112b therein. As discussed in further detail below, once the extended tabs 112a and 112b are fully positioned within the rails 104a and 104b and the head 114 is positioned within the tip 106, the handles 102a and 102b can be operated, one at a time, to break the extended tabs 112a and 112b from the head 114. In other examples, the handles 102a and 102b can be operated simultaneously to break the extended tabs 112a and 112b from the head 114. The tab breaker 101 and the extended tabs 112 can be together removed, such as from a cavity or opening during a procedure.

FIG. 2 illustrates a focused isometric view of the tab breaker system 100 FIG. 2 also shows orientation indicators Proximal and Distal. The tab breaker system 100 can be consistent with the system 100 of FIGS. 1A-1C. FIG. 2 shows additional details. For example, FIG. 2 shows that the anchor 110 can include a shank 116, that the head 114 can define an anchor slot 118, and that the head 114 can include breakaway portions 120a and 120b.

The shank 116 can be connected to a distal portion of the head 114 with the shank 116 extending distally therefrom and where the axis A can be a central axis for the head 114 and the shank 116. In other examples, the shank can deviate from the axis A at various angles. The shank 116 can be a threaded shank or screw including male threads configured to engage bone, such as a relatively coarse thread pattern. In some examples, the shank 116 can be configured to threadably secure to a vertebra of a spine of a human. The shank 116 can be an integral component to the head 114 in some examples, coupled to a distal portion of the head 114. In other examples, the shank 116 can be a portion of a fastener that is a separate component from the head 114 and can be disposed within a bore of the head 114 and configured to be retained therein.

The anchor slot 118 of the anchor 110 can be generally U-shaped, in some examples, and can be configured to receive a connecting member (such as a connecting rod or wire) therethrough. In some examples, the head 114 can have flat sides and one or more tool interfaces.

The breakaway portions 120a and 120b can be a portion of the anchor 110 coupling the head 114 to the extended tabs 112A and 112B, respectively, where the breakaway portions 120 can have a thickness that is smaller than a thickness of the head 114 or the extended tabs 112A and 112B (only tab 112B is visible in FIG. 2) that surrounds the breakaway portions 120a and 120b. The reduced thickness of the breakaway portions 120a and 120b can facilitate separation and removal of the extended tabs 112A and 112B from the head 114.

FIG. 2 also shows that the rail 104a can include tracks 122a and 122b. The rail 104b can include tracks 124a and 124b. The tracks 122a and 122b can extend outward from the axis A and can extend inward towards each other to, at least in part, define a channel 126. The channel 126 can be configured to receive the extended tab 112a therein. The tracks 122a and 122b can terminate prior to making contact such that the tracks 122a and 122b define a slot 127 extended through the tracks 122a and 122b at a laterally outer portion of the rail 104a. In some examples, the slot 127 can be used for extraction of the extended tab 112a following separation of the tab 112a from the head 114 and following removal of the tab 112a from the opening or cavity.

FIG. 2 further shows that the tip 106 can include a collar 128 and a pillar 132. The collar 128 can be configured to receive the head 114 of the anchor 110 at least partially therein. The collar 128 can include a tip slot 130 (or notch 130). The tip slot 130 can be generally U-shaped, in some examples. The tip slot 130 can be located on the collar such that when the extended tabs 112 are positioned within the rails 104, the tip slot 130 aligns with the anchor slot 118. The tip slot 130 can be positionable around a connecting member, which can be positioned within the anchor slot 118.

The pillar 132 can extend substantially proximally from the collar 128 and can be configured to receive and support the pivot 108 therein, where the pivot 108 can be a fastener such as a pin, screw, boss, or the like. The rails 104 can be connected to the pillars 132 (only one pillar is visible in FIG. 2) via the pivot 108 to allow the rails 104 to pivot or rotate with respect to the pillars 132, the tip 106, and the anchor 110. Such pivoting or rotation of the rails 104 can allow the extended tabs 112a and 112b to be separated from the head 114 at the breakaway portions 120a and 120b, respectively, as shown in FIGS. 3A and 3B below.

Figure 3A:
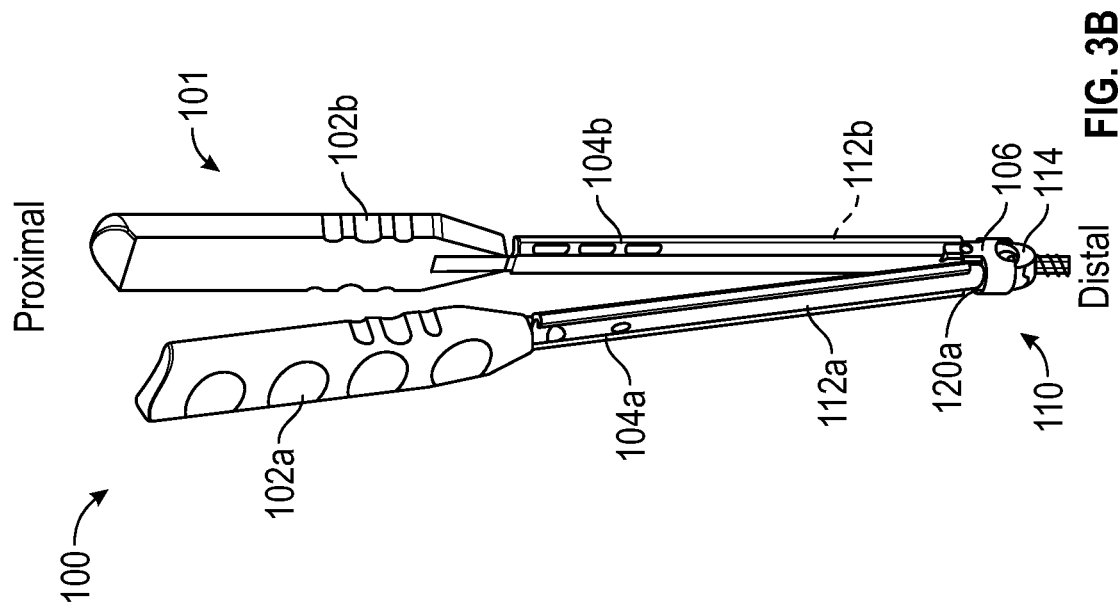
FIG. 3A illustrates an isometric view of a tab breaker system in a first position.

FIG. 3A illustrates an isometric view of the tab breaker system 100 in a first position. FIG. 3B illustrates an isometric view of the tab breaker system 100 in a second position. FIGS. 3A-3B also show orientation indicators Proximal and Distal. The tab breaker system 100 of FIGS. 3A and 3B can be consistent with the tab breaker system 100 discussed above with respect to FIGS. 1-2A; FIGS. 3A-3B show additional steps of how the tab breaker 101 can be operated.

Once the extended tabs 112a and 112b are positioned within the rails 104a and 104b, respectively, and once the head 114 is positioned within the tip 106, as shown in FIG. 2 above, the handles 102 can be operated to break the extended tabs 112a and 112b. As shown in FIG. 3A. the first handle 102a can be held in place and the second handle 102b can be moved outward from the first handle 102a such that the handle 102b and the rail 104b pivot about the pivot 108 bending the extended tab 112b with respect to the head 114 at the breakaway portion 120b. When the extended tab 112b is bent sufficiently far with respect to the head 114, the tab 112b can separate from the head 114 and can be retained within the rail 104b. The second handle 102b can then be returned to an upright position, as shown in FIG. 3B.

Figure 3B:
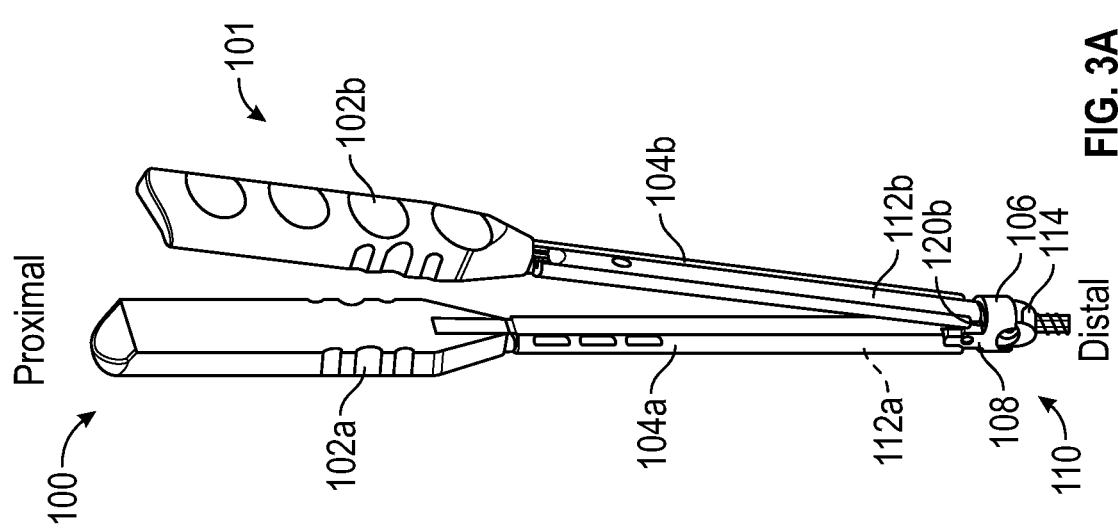
FIG. 3B illustrates an isometric view of a tab breaker system in a second position.

With both handles 102 upright, the second handle 102b can be held in the upright position and the first handle 102a can be operated, as shown in FIG. 3B. The first handle 102a can be moved outward from the second handle 102b such that the handle 102a and the rail 104a pivot about the pivot 108 bending the extended tab 112a with respect to the head 114 at the breakaway portion 120a. When the extended tab 112a is bent sufficiently far with respect to the head 114, the tab 112a can separate from the head 114 and can be retained within the rail 104a. The handle 102a can then be returned to an upright (and optionally locked position) and the extended tabs 112a and 112b can be extracted from the opening or cavity along with the tab breaker 101. The tabs 112 can then be removed from the tab breaker 101. Such a process can be repeated on multiple anchors, such as during a spinal stabilization procedure.

Figure 4B:
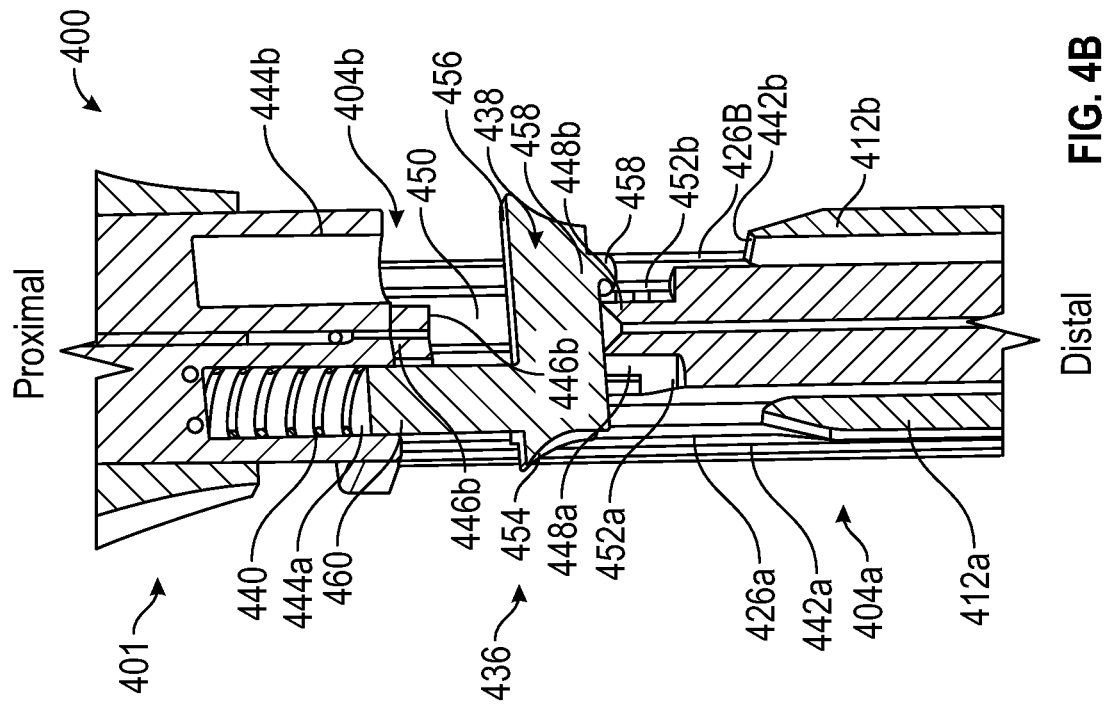
FIG. 4B illustrates a cross-sectional isometric view of a tab breaker system.
Figure 4A:
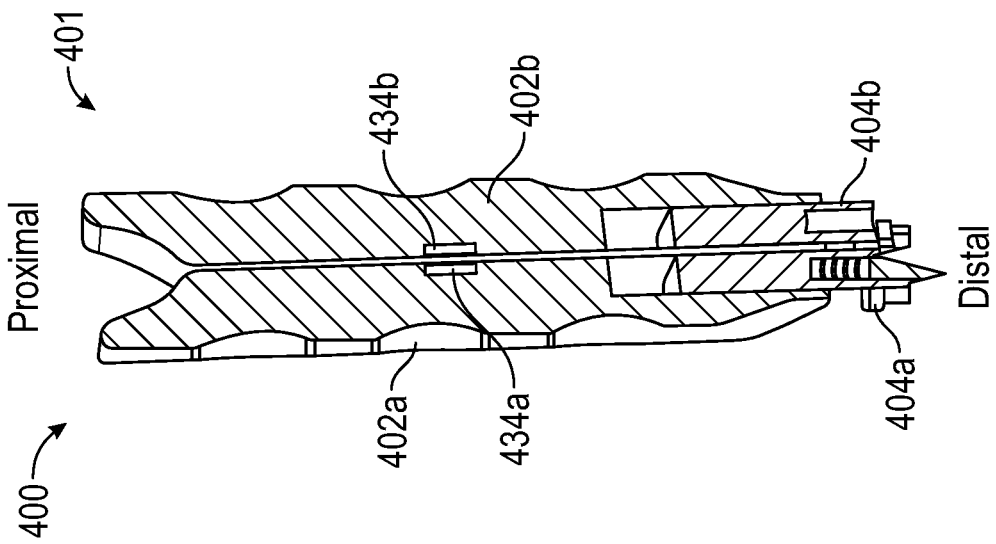
FIG. 4A illustrates a cross-sectional isometric view of a tab breaker system.

FIG. 4A illustrates a cross-sectional isometric view of a tab breaker system 400. FIG. 4B illustrates a cross-sectional isometric view of the tab breaker system 400. FIGS. 4A-14 also show orientation indicators Proximal and Distal. FIGS. 4A and 4B are discussed together below. The tab breaker system 400 can be similar to the tab breaker system 100 discussed above. Any of the tab breakers discussed herein can be modified to include the features of the tab breaker system 400.

The tab breaker system 400 can include a tab breaker 401 including handles 402a and 402b and rails 404a and 404b. The handle 402a can include a magnet 434a and the handle 402b can include a magnet 434b. The magnets 434a and 434b can be oriented within the handles 402a and 402b such that a portion of the magnet 434a has a polarity that is opposite to a polarity of a portion of the magnet 434b that is facing the portion of the magnet 434a. Such an orientation can allow the magnets 434 to magnetically couple when the handles 402 are in contact or are in close proximity. The magnets 424 can be sized to retain the handles 402 in a closed position and to retain the first rail 404a and the second rail 404b in the first upright position and the second upright position, respectively, such that a force is required to separate the handles 402.

FIG. 4B shows that the tab breaker 401 can include a locking assembly 436. The locking assembly 436 can be configured to lock the handles 402 and the rails 404 together and can be operable to allow the handles 402 and the rails 404 to separate. Any of the tab breakers discussed herein can be modified to include such a locking assembly.

The locking assembly 436 can include a lock 438 and a biasing element 440. The rails 404a and 404b can include slots 426a and 426b, respectively, and can be configured to receive extended tabs 412a and 412b, respectively, therein. The extended tabs 412a and 412b can include proximal tips 442a and 442b, which can be proximal ends, terminations, or proximal portions of the extended tabs 412a and 412b, respectively.

The rails 404a and 404b can also include bores 444a and 444b, which can be configured to receive the biasing element 440 therein. The biasing element 440 can be a spring or other biasing member such as a compression coil spring. In other examples, biasing element 440 can be other springs or resilient members, such as a wave spring or compressible and resilient members comprised of resilient materials such as rubbers, plastic, and the like. The biasing element 440 can be positioned within the bore 444a of the rail 404a. In other examples, the biasing element can be positioned in the bore 444b (and thereby connected to the rail 404a and the handle 402a). The rails 404a and 404b can be manufactured such that a single component can be used to be either the rail 404a or the rail 404b.

The rails 404a and 404b can also include lock projections 446a and 446b and 448a and 448b that can together define a lock opening 450 extending through the rails 404a and 404b. The rails 404a and 404b can further include recesses 452a and 452b, respectively, that can interact with portions of the lock 438.

The lock 438 can include ledges 454 and 456, a latch 458, and a guide rod 460. The lock 438 can be positioned between the proximal lock projections 446a and 446b and the distal lock projections 448a and 448b in the lock opening 450 such that the lock 438 can translate within the lock opening 450. Translation of the lock 438 within the lock opening 450 can be limited proximally by contact between the lock 438 and the proximal projections 446 and can be limited distally by contact between the lock 438 and the distal projections 448.

The ledges 454 and 456 can extend beyond laterally outer surfaces of the rails 404a and 404b, respectively to allow a user to engage the ledges 454 and 456 for movement of the lock 438 with respect to the rails. In some examples, the ledges 454 and 456 can form a partial or complete ring around one or more of the rails 404. The guide rod 460 can extend proximally into the bore 444a and can engage the biasing element 440 such that the biasing element 440 can bias the lock 438 distally. The distal bias can cause the latch 458 to be positioned (in a biased state of the lock 436) into the recess 452b, distal of the projection 448b. The projection 448b can serve as a catch for the latch 458, which can help to limit movement of the lock 436 away from the rail 404b, which can therefore limit movement of the rail 404a away from the rail 404b when the rails 404 are in the upright or locked position.

During operation of the tab breaker 401, when it is desired to separate the handles 402 and rails 404, one or more of the ledges 454 or 456 can be actuated proximally to overcome a bias force of the biasing element 440 and to move the latch 458 proximal of the projection 448b, which can allow the arm 404a to be moved laterally (or pivotably) away from the arm 404b. This can help prevent the rails 404 (and handles) 402 from separating when it is desired to have them together, such as during insertion of the tab breaker 401 into an opening or cavity.

Such a release of the lock 436 can also be performed by the extended tabs 412, such as when the extended tabs 412 are translated proximally into the channels 426. When a head of the anchor (such as the head 114) is fully seated in a tip of the tab breaker 401 (such as the tip 106), the proximal tip 442b can contact the lock 436 to cause the lock 436 to translate proximally, releasing the latch 458 proximal of the projection 448b, and allowing the rails 404a and 404b to move relative to each other.

When it is desired to lock the rails 404 together, the rails 404 can be brought together until the latch 458 engages the projection 448b. The projection 448b can include a ramped (or chamfered or curved or angled) surface to cause the latch 458 to move the lock 436 proximally to clear the projection 448b. Once the latch 458 clears the projection 448b, the biasing element 440 can force the latch 458 distally, placing the lock 436 in a locked position where the latch 458 cannot move laterally away from the rail 404b until it is moved proximally again to an unlocked position.

Figure 5:
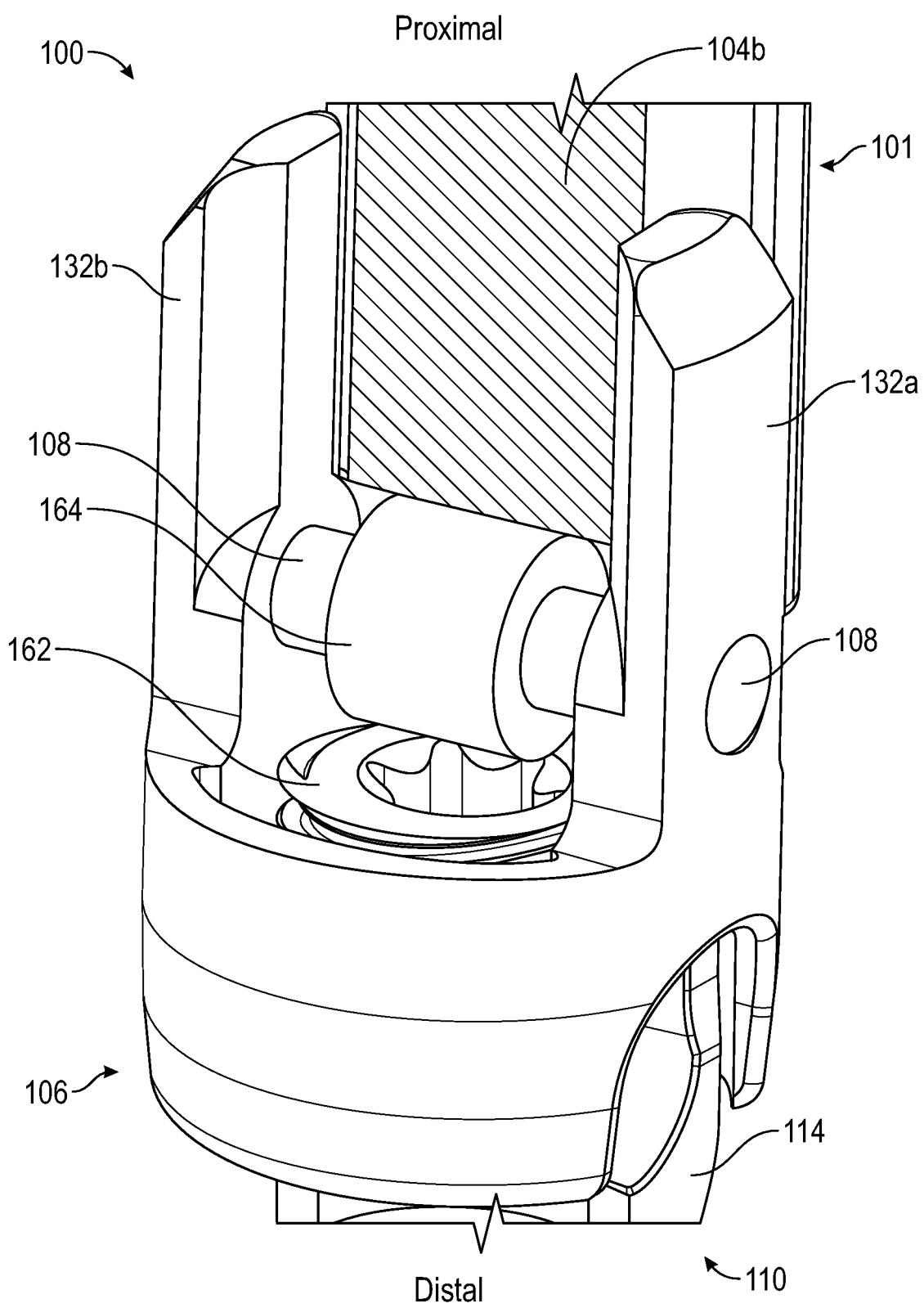
FIG. 5 illustrates an isometric view of a portion of a tab breaker system.
Figure 6:
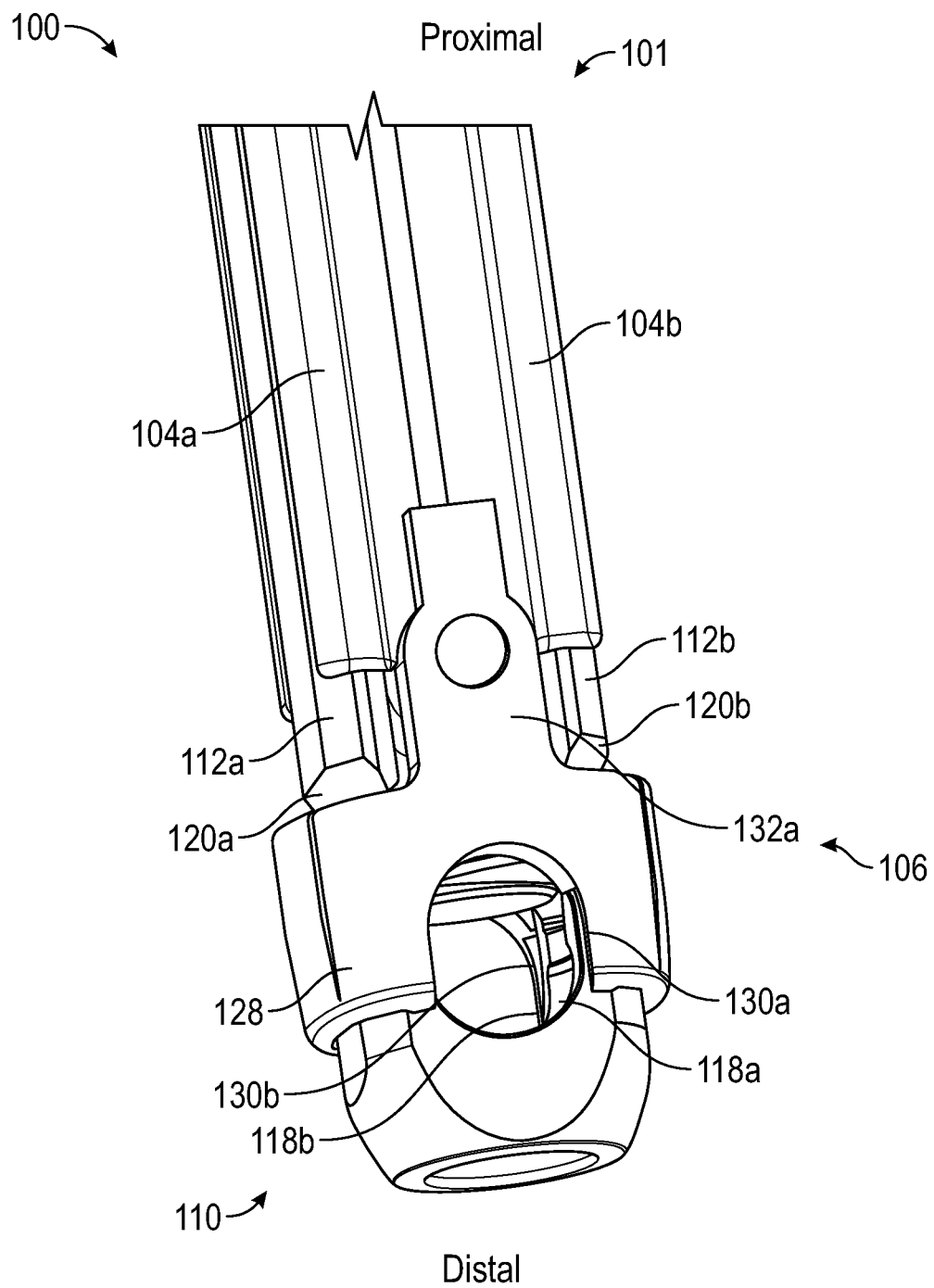
FIG. 6 illustrates an isometric view of a portion of a tab breaker system.

FIG. 5 illustrates an isometric view of a portion of the tab breaker system 100. FIG. 6 illustrates an isometric view of a portion of the tab breaker system. FIGS. 5 and 6 also show orientation indicators Proximal and Distal. FIGS. 5 and 6 are discussed below together The tab breaker system 100 of FIGS. 5 and 6 can be consistent with the tab breaker system 100 of FIGS. 1A-3B. FIG. 5 shows that the tab breaker system can include a set screw 162 (or closure top) which can be threadably securable to the head 114 such as to retain a connection member within the head 114. The pivot 108 can be positioned such the rails 104 do not contact the set screw 162.

FIG. 5 also shows that the pivot 108 can be a pin supported by and connected to the pillars (or uprights) 132a and 132b. FIG. 5 further shows that the rail 104b can include a knuckle 164 which can connect the rail 104b to the pivot 108 and can allow for rotational movement of the rail 104b about the pivot 108. The rail 404a can also include knuckles connecting the rail 404a to the pivot 108, such as knuckles positioned on either side of the knuckle 164.

FIG. 6 shows how tip slots 130a and 130b can be located on the collar 128 such that when the extended tabs 112 are positioned within the rails 104, the tip slots 130a and 130b align with anchor slots 118a and 118b, respectively. The tip slots 130 can be positionable at least partially around a connecting member or rod, which can be positioned within the anchor slots 118 to extend through the housing 114 of the anchor 110.

Figure 7:
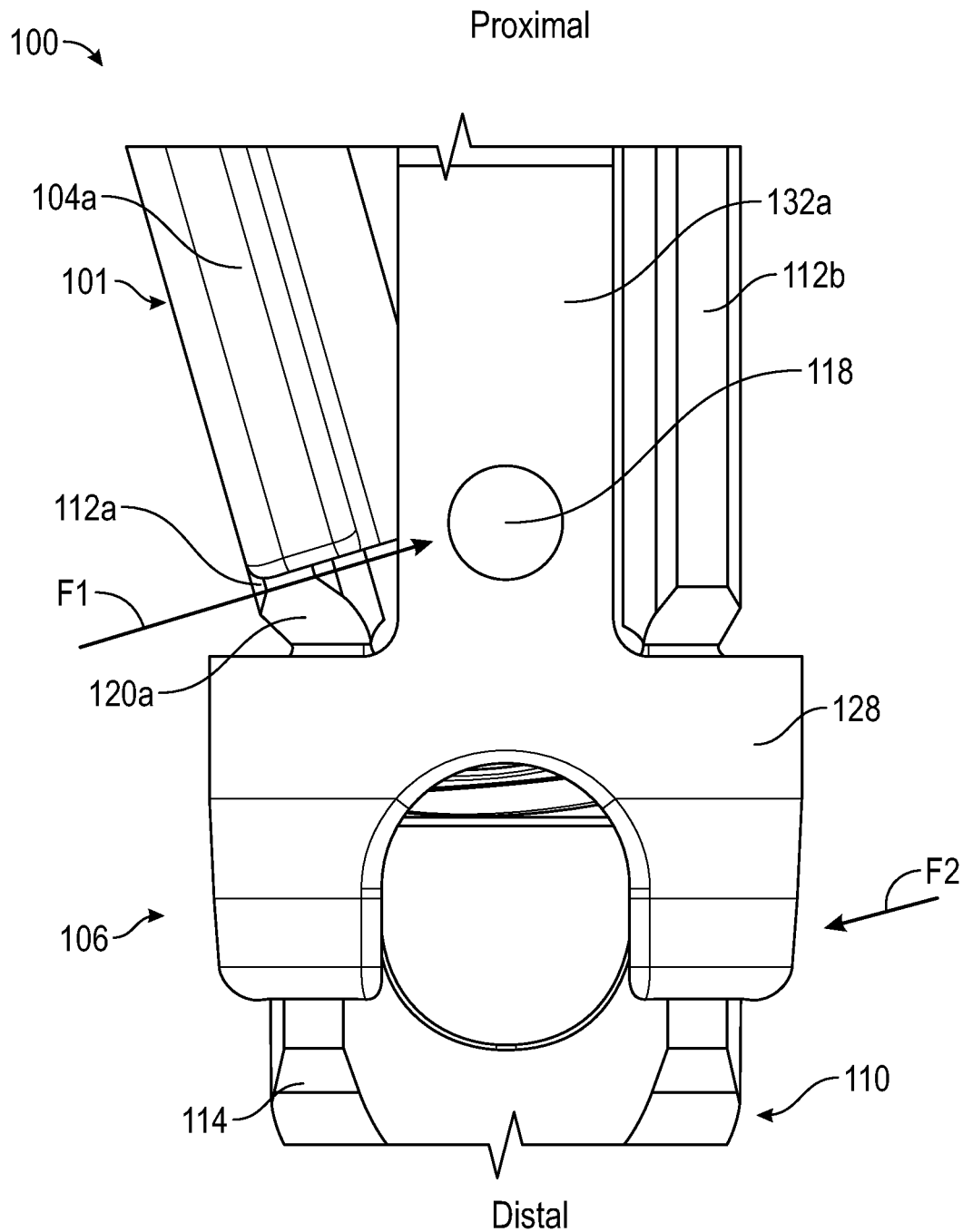
FIG. 7 illustrates an isometric view of a portion of a tab breaker system.

FIG. 7 illustrates an isometric view of a portion of the tab breaker system 100. FIG. 7 also shows orientation indicators Proximal and Distal. The tab breaker system 100 of FIG. 7 can be consistent with the tab breaker system 100 discussed above. FIG. 7 shows how forces F1 and F2 balance to apply leverage to extended tabs.

As shown in FIG. 7, when the rail 104a is rotated away from the pillar 132a, a force can be generated by the handle (such as the handle 102a) and can create a reaction force, F1, which can be applied by the rail 104a to the pivot 108 and by the extended tab 112a to the housing 114 and collar 128. Because the collar 128 can be engaged with the head 114 of the anchor, the reaction force F1 can create a reaction force F2 generated between the head 114 and the collar 128, which can help to prevent movement of the tip 106 with respect to the extended tab 112a during breaking of the tab 112a from the head 114. These forces can allow a user to generate larger forces on the extended tab 112a using the tab breaker 101. Further, the second handle 102b can be held in an upright position during breaking of the extended tab 112a to further help to limit movement of the tip 106 to further help to increase forces applied to the extended tab 112 during breaking. Because relatively larger forces can be applied, relatively stiffer tabs can be used, which can help reduce undesired separation of the extended tabs from the head 114 during a procedure.

FIG. 8 illustrates a cross-sectional isometric view of a portion of the tab breaker system 100. FIG. 8 also shows orientation indicators Proximal and Distal. The tab breaker system 100 of FIG. 8 can be consistent with the tab breaker system 100 discussed above. FIG. 8 shows how the rails 104 can interact with the pillars 132.

The rail 104a can include chamfers 166a and 166b located at laterally inner portions of the rail 104a. The rail 104b can also include chamfers. The pillars 132a and 132b can include pillar chamfers 168a and 168b, respectively. The rail chamfers 166a and 166b can be configured to contact the pillar chamfers 168a and 168b, respectively, when the rail 104a is in the upright position. The chamfers 166 and 168 can help to increase a contact area between the rails 104 and the pillars 132.

Figure 9B:
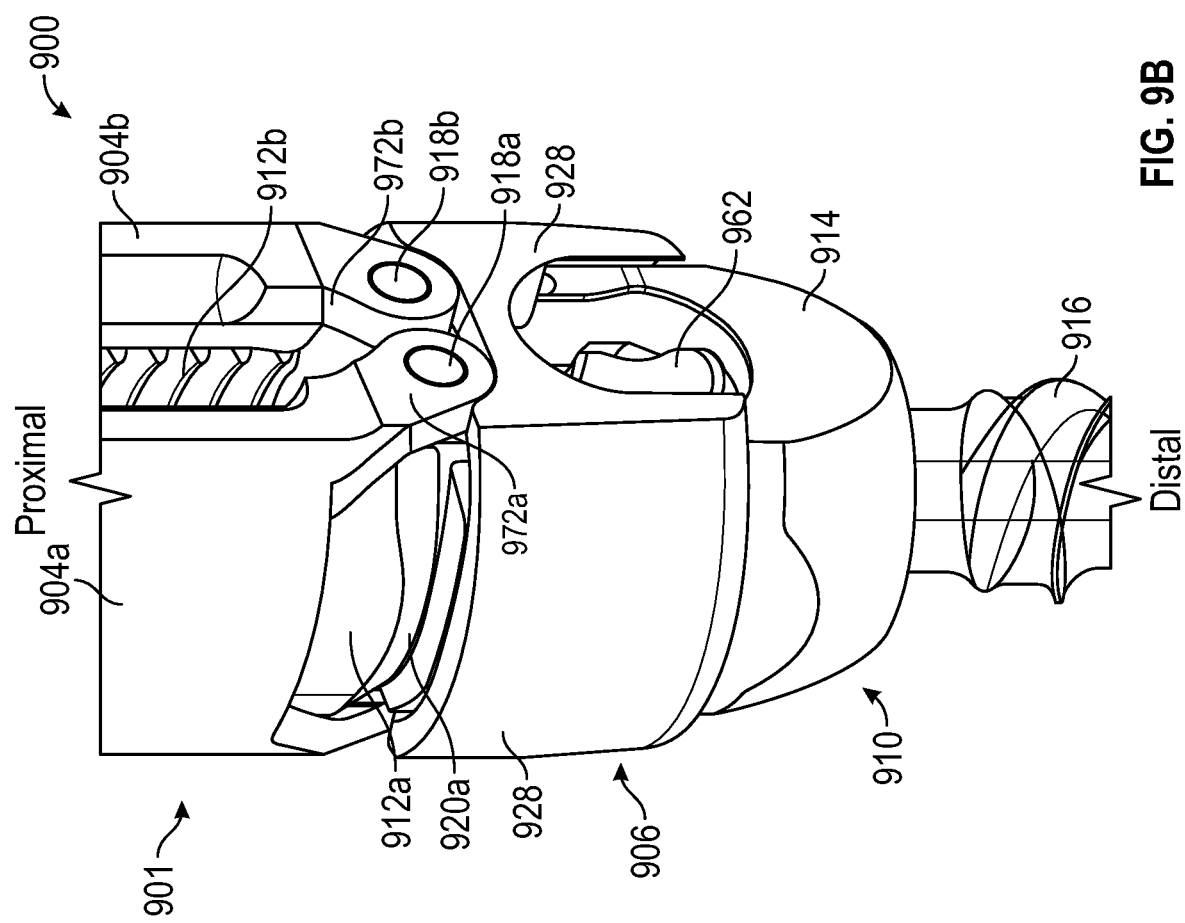
FIG. 9B illustrates an isometric view of a tab breaker system.
Figure 9A:
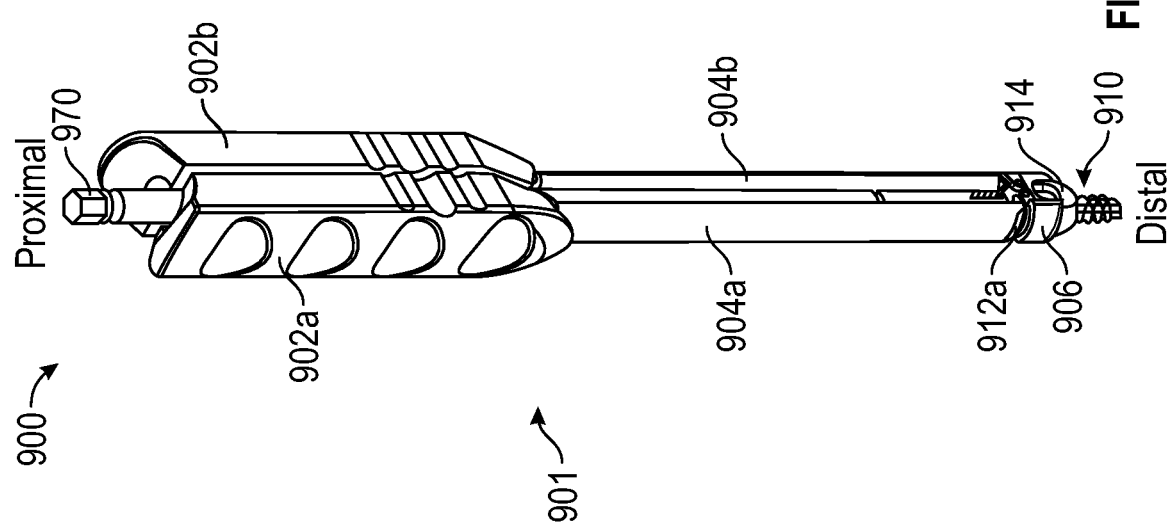
FIG. 9A illustrates an isometric view of a tab breaker system.

FIG. 9A illustrates an isometric view of a tab breaker system 900. FIG. 9B illustrates an isometric view of the tab breaker system 900. FIGS. 9A-9B also show orientation indicators Proximal and Distal. The tab breaker system 900 can include externally mounted rails, which can allow for passing of instruments between the arms and into the anchor. Any of the previously discussed tab breakers can be modified to include these components.

FIG. 9A shows that the tab breaker system 900 can include a tab breaker 901 and an anchor 910. The anchor 910 can include extended tabs 912a and 912b and a head 914. The tab breaker 901 can include handles 902a and 902b, rails 904a and 904b and a tip 906. As shown in FIG. 9A, a device, such as a driver 970 can be positioned proximally to distally between the handles 902 and between the rails 904 such that the driver 970 extends into the head 914 of the anchor 910. The driver 970 can be used to secure a set screw (such as a set screw 962 of FIG. 9B) to the head 914. Once the set screw 962 is secured to the head 914, the driver 970 can be removed and the handles 902 can be operated to break the extended tabs 912 from the head 914, thereby allowing the tab breaker 901 to be used in multiple steps of an alignment or fusion procedure.

FIG. 9B shows how the rails 904 can connect to the tip 906. The rail 904a can include a set of knuckles 972a and the rail 904b can include a set of knuckles 972b. The knuckles 972a can be connected to the tip 906 using pivots 918a outward of the extended tab 912a. Similarly, the knuckles 972b can be connected to the tip 906 using pivots 918b outward of the extended tab 912b. Because the rails 904 are connected to an outer portion of a collar 928 of the tip 906, the driver 970 can extend between the rails 904 to within the head 914 to engage the set screw 962.

NOTES AND EXAMPLES

The following, non-limiting examples, detail certain aspects of the present subject matter to solve the challenges and provide the benefits discussed herein, among others.

Example 1 is a tool for breaking tabs of a vertebral bone anchor, the tool comprising: a tip positionable over a housing of a vertebral bone anchor; a first rail pivotably coupled to the tip and extending proximally away from the tip, the first rail configured to receive a first extended tab therein, and the first rail pivotable with respect to the tip between a first upright position and a first outward position to break the first extended tab from the housing; and a second rail pivotably coupled to the tip and extending proximally away from the tip, the second rail configured to receive a second extended tab therein, and the second rail pivotable with respect to the tip to between a second upright position and a second outward position to break the second extended tab from the housing.

In Example 2, the subject matter of Example 1 optionally includes a first handle connected to a proximal portion of the first rail; and a second handle connected to a proximal portion of the second rail.

In Example 3, the subject matter of Example 2 optionally includes a first magnet located on the first handle; and a second magnet located on the second and couplable with the first magnet to retain the first rail and the second rail in the first upright position and the second upright position, respectively.

In Example 4, the subject matter of any one or more of Examples 2-3 optionally include a lock connected to the first handle and movable between a locked position where the lock engages the second handle to lock the first rail and the second rail in the first upright position and between an unlocked position where the first rail and the second rail are movable with respect to each other.

In Example 5, the subject matter of Example 4 optionally includes a spring connected to the first handle and engaged with the lock, the spring configured to bias the lock to the locked position.

In Example 6, the subject matter of any one or more of Examples 4-5 optionally include wherein the first extended tab is engageable with the lock to move the lock to the unlocked position when the tip is position over the housing.

In Example 7, the subject matter of any one or more of Examples 1-6 optionally include wherein the tip includes a notch configured to at least partially surround a connecting rod extending at least partially through the housing of the vertebral bone anchor.

In Example 8, the subject matter of any one or more of Examples 1-7 optionally include a pillar connected to the tip and extending proximally therefrom, the first rail and the second rail pivotably coupled to the pillar.

In Example 9, the subject matter of Example 8 optionally includes a second pillar connected to the tip and extending proximally therefrom, the first rail and the second rail pivotably coupled to the second pillar.

In Example 10, the subject matter of Example 9 optionally includes a pivot pin extending between the first pillar and the second pillar, the first rail and the second rail pivotably coupled to the pivot pin.

In Example 11, the subject matter of Example 10 optionally includes wherein the first rail includes a knuckle connected to a distal portion of the first rail, the knuckle pivotably coupled to the pivot pin.

In Example 12, the subject matter of any one or more of Examples 8-11 optionally include wherein the first rail includes a rail chamfer configured to engage a pillar chamfer to limit movement of the first rail toward the second rail.

In Example 13, the subject matter of any one or more of Examples 1-12 optionally include wherein the first rail defines a channel configured to receive the first extended tab therein and wherein the second rail defines a channel configured to receive the second extended tab therein.

In Example 14, the subject matter of Example 13 optionally includes wherein the first channel includes a slot extending through a laterally outer portion of the first rail.

Example 15 is a tool for breaking tabs of a vertebral bone anchor, the tool comprising: a tip positionable over a housing of a vertebral bone anchor; a first rail connected to the tip and extending proximally away from the tip, the first rail configured to receive a first extended tab therein, and the first rail pivotable with respect to the tip between a first upright position and a first outward position; and a second rail connected to the tip and extending proximally away from the tip, the second rail configured to receive a second extended tab therein, and the second rail pivotable with respect to the tip to between a second upright position and a second outward position.

In Example 16, the subject matter of Example 15 optionally includes a first handle connected to a proximal portion of the first rail; and a second handle connected to a proximal portion of the second rail.

In Example 17, the subject matter of Example 16 optionally includes a first magnet located on the first handle; and a second magnet located on the second and couplable with the first magnet to retain the first rail and the second rail in the first upright position and the second upright position, respectively.

In Example 18, the subject matter of any one or more of Examples 16-17 optionally include a lock connected to the first handle and movable between a locked position where the lock engages the second handle to lock the first rail and the second rail in the first upright position and between an unlocked position where the first rail and the second rail are movable with respect to each other.

In Example 19, the subject matter of Example 18 optionally includes a spring connected to the first handle and engaged with the lock, the spring configured to bias the lock to the locked position.

Example 20 is a method of operating a tool for breaking tabs of an anchor, the method comprising: inserting a first extended tab of the anchor into a first rail and a second extended tab of the anchor into the second rail; translating a tip of the tool connected to the first rail and the second rail distally; engaging a housing of the anchor with the tip; pivoting the first rail with respect to the tip and the second rail to separate the first extended tab from the housing; and pivoting the second rail with respect to the tip and the first rail to separate the second extended tab from the housing.

Example 21 is a tool for breaking tabs of a vertebral bone anchor, the tool comprising: a tip positionable over a housing of a vertebral bone anchor; a first rail pivotably coupled to the tip and extending proximally away from the tip, the first rail configured to receive a first extended tab therein, and the first rail pivotable with respect to the tip between a first upright position and a first outward position to break the first extended tab from the housing; and a second rail coupled to the tip and extending proximally away from the tip, the second rail configured to receive a second extended tab therein.

In Example 22, the subject matter of Example 21 optionally includes a first handle connected to a proximal portion of the first rail; and a second handle connected to a proximal portion of the second rail.

In Example 23, the subject matter of Example 22 optionally includes a first magnet located on the first handle; and a second magnet located on the second and couplable with the first magnet to retain the first rail and the second rail in the first upright position and the second upright position, respectively.

In Example 24, the subject matter of any one or more of Examples 22-23 optionally include a lock connected to the first handle and movable between a locked position where the lock engages the second handle to lock the first rail and the second rail in the first upright position and between an unlocked position where the first rail and the second rail are movable with respect to each other.

In Example 25, the subject matter of Example 24 optionally includes a spring connected to the first handle and engaged with the lock, the spring configured to bias the lock to the locked position.

In Example 26, the apparatuses or method of any one or any combination of Examples 1-25 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for breaking tabs of a vertebral bone anchor, comprising:
    positioning a tip over a housing of a vertebral bone anchor and first and second rails over first and second extended tabs joined to the vertebral bone anchor housing by first and second breakaway portions, respectively, the tip being pivotably connected to the first and second rails and extending proximally away from opposing sides of an anchor slot of the vertebral bone anchor and comprising a collar configured, during breakage and removal of the first and second extended tabs from the anchor slot, to at least substantially enclose opposing sides of the anchor slot of the vertebral bone anchor housing distally from the first and second breakaway portions; and
    pivoting the first and second rails with respect to the tip from different first and second upright positions, respectively, to different first and second outward positions, respectively, to break the first and second extended tabs from the housing.

2. The method of claim 1, wherein the anchor slot is U-shaped, wherein the tip further comprises a tip slot configured to align with the anchor slot in the vertebral bone anchor housing and be positionable around a connecting member positioned within the anchor slot and wherein a first handle is connected to a proximal portion of the first rail and a second handle is connected to a proximal portion of the second rail.

3. The method of claim 2, wherein the collar is configured, during breakage of the first and second extended tabs, to enclose at least most of the opposing sides of the anchor slot of the vertebral bone anchor housing and wherein a first magnet is located on the first handle and a second magnet is located on the second handle and couplable with the first magnet to retain the first rail and the second rail in the first upright position and the second upright position, respectively.

4. The method of claim 2, wherein a lock is connected to the first handle and movable between a locked position where the lock engages the second handle to lock the first rail and the second rail in the first upright position and between an unlocked position where the first rail and the second rail are movable with respect to each other.

5. The method of claim 4, wherein a spring is connected to the first handle and engaged with the lock, the spring configured to bias the lock to the locked position.

6. The method of claim 4, wherein the lock is positioned to engage the first extended tab to move the lock to the unlocked position when the tip is position over the housing.

7. The method of claim 1, wherein the collar is configured, during breakage of the first and second extended tabs, to enclose at least most of the opposing sides of the anchor slot of the vertebral bone anchor housing, and wherein the tip includes a notch configured to at least partially surround a connecting rod extending at least partially through the anchor slot of the housing of the vertebral bone anchor.

8. The method of claim 1, wherein a first pillar is connected to the tip and extending proximally therefrom, the first rail and the second rail pivotably coupled to and contacting opposing chamfers in the first pillar.

9. The method of claim 8, wherein a second pillar is connected to the tip and extending proximally therefrom, the first rail and the second rail pivotably coupled to and contacting opposing chamfers in the second pillar.

10. The method of claim 9, wherein a pivot pin extends between the first pillar and the second pillar, the first rail and the second rail pivotably coupled to the pivot pin.

11. The method of claim 10, wherein the first rail includes a knuckle connected to a distal portion of the first rail, the knuckle pivotably coupled to the pivot pin.

12. The method of claim 8, wherein the first rail includes a rail chamfer configured to engage the pillar chamfer to limit movement of the first rail toward the second rail.

13. The method of claim 1, wherein, during breakage of the first and second extended tabs, the first and second breakaway portions are positioned between at least a portion of the collar and at least a portion of the first and second rails, wherein the first rail defines a first channel configured to receive the first extended tab therein and wherein the second rail defines a second channel configured to receive the second extended tab therein and wherein the first and second rails are configured to remain in a constant axial position relative to the tip when receiving corresponding first and second extended tabs.

14. The method of claim 13, wherein the first channel includes a slot extending through a laterally outer portion of the first rail.

15. A method for breaking tabs of a vertebral bone anchor, comprising:

positioning a tip over a housing of a vertebral bone anchor and first and second rails over first and second extended tabs, respectively, joined to the vertebral bone anchor housing by first and second breakaway portions, respectively, and extending proximally away from opposing sides of an anchor slot of the vertebral bone anchor, the tip comprising a collar configured to at least substantially enclose opposing sides of the anchor slot of the vertebral bone anchor housing during breakage of the first and second extended tabs, wherein the first and second rails are connected to the tip and extend proximally away from the tip and each of the first and second rails is pivotable with respect to the tip between respective first and second upright positions and first and second outward positions; and moving the first and second rails from the respective first and second upright positions to the respective first and second outward positions to break the first and second extended tabs away from the vertebral bone anchor housing, and wherein, during breakage of the first and second extended tabs, the first and second breakaway portions are positioned between at least a portion of the collar and at least a portion of the first and second rails.

16. The method of claim 15, wherein the tip further comprises a tip slot configured to align with the anchor slot in the vertebral bone anchor housing and be positionable around a connecting member positioned within the anchor slot and wherein a first handle is connected to a proximal portion of the first rail; and a second handle connected to a proximal portion of the second rail.

17. The method of claim 16, wherein a first magnet is located on the first handle and a second magnet is located on the second handle and couplable with the first magnet to retain the first rail and the second rail in the first upright position and the second upright position, respectively.

18. The method of claim 16, wherein a lock is connected to the first handle and movable between a locked position where the lock engages the second handle to lock the first rail and the second rail in the first upright position and between an unlocked position where the first rail and the second rail are movable with respect to each other.

19. The method of claim 18, wherein a spring is connected to the first handle and engaged with the lock, the spring configured to bias the lock to the locked position.

20. The method of claim 15, wherein the anchor slot is U-shaped and wherein the collar is configured, during breakage of the first and second extended tabs, to enclose at least most of the opposing sides of the anchor slot of the vertebral bone anchor housing.

* * * * *